US00PP10464P

United States Patent [19]

Challet

[11] Patent Number: Plant 10,464

[45] Date of Patent: Jun. 23, 1998

[54] CHRYSANTHEMUM PLANT NAMED 'CHABAXO'

[75] Inventor: Jean Pierre Challet, Nuaille, France

[73] Assignee: Selection New Plant Sarl, Le Luc, France

[21] Appl. No.: 772,900

[22] Filed: Dec. 24, 1996

[51] Int. Cl.[6] ..... A01H 5/00

[52] U.S. Cl. ..... Plt./78

[58] Field of Search ..... Plt./78

*Primary Examiner*—Howard J. Locker
*Attorney, Agent, or Firm*—Burns, Doane, Swecker & Mathis, L.L.P.

[57] ABSTRACT

A new and distinct Chrysanthemum cultivar named 'Chabaxo' is provided. The new cultivar was the result of a controlled breeding program. Attractive yellow double blossoms are formed in profusion as a round ball surrounding the plant. Recurrent flower production throughout the year is possible. The response period of the flowers is approximately eight weeks. When using natural flowering production, the resulting flowers from a distance resemble those having a spider form which is attributable to variation in the lengths and configurations of the ray florets. The plant possesses relatively soft stems, forms attractive dark green leaves, and commonly assumes a height of approximately 25 to 30 cm. The bright yellow blossom coloration contrasts nicely with the dark green foliage. The new cultivar is particularly well suited for use in the production of a decorative pot Chrysanthemum. No growth regulator is required to achieve the relatively short plant height.

2 Drawing Sheets

SUMMARY OF THE INVENTION

The present invention comprises a new and distinct cultivar of Chrysanthemum, botanically known as *Dendranthema grandiflora,* and hereinafter is referred to by the cultivar name 'Chabaxo'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during November, 1986, at Nuaille, Trementines, France. The female parent (i.e., the seed parent) was the 'Fada' cultivar (non-patented in the United States) which was bred by a French breeder named Bernard, having double purple flat flowers, tubular ray florets, and which could be grown only in a natural production cycle, and the male parent (i.e., the pollen parent) was the 'Domi' cultivar (non-patented in the United States) which was an old French variety having small honey-colored anemone flowers. The parentage of the new cultivar can be summarized as follows:

'Fada'×'Domi'.

The seeds resulting from the above pollination were sown and many small plants were obtained which were physically biologically different from each other. Selective study resulted in the identification of a single plant of the new cultivar.

It was found that the new cultivar of the present invention:

(a) exhibits in profusion attractive decorative double yellow blossoms,
(b) is highly amenable to branching by pinching,
(c) forms attractive foliage,
(d) achieves a short plant height, and
(e) is particularly well suited for flowering as a pot mum on a recurrent basis throughout the year.

The new cultivar is intended primarily as a decorative pot Chrysanthemum for growing outdoors at temperatures above freezing. However, the new cultivar also can be grown indoors.

In the absence of debudding approximately 7 to 9 blossoms commonly form per stem. Also, the new cultivar can be grown as a disbud to form striking blooms. An increased number of branches readily can be induced by pinching. The pinching of a cutting commonly produces approximately 6 to 9 stems per cutting. No growth regulator is required to produce the short plant height; however, a growth regulator optionally can be utilized.

The new cultivar can be considered to be an October-flowering greenhouse variety with the natural flowering season commonly occurring in weeks 42 to 43 of the year. The blossoms are long-lasting and commonly can be maintained on the plant for approximately three weeks.

Asexual reproduction of the new cultivar by cuttings taken during 1988, as performed in Nuaille, Trementines, France, in a controlled environment has demonstrated that the characteristics of the new cultivar as herein described are firmly fixed and are retained through successive generations of asexual propagation.

'Chabaxo' has not been observed under all possible environmental conditions to date. Accordingly, it is possible that the phenotype may vary somewhat with variations in the environment, such as temperature, light, day length, contact with pesticides and/or subjection to growth retardant treatments.

The new 'Chabaxo' cultivar is being marketed under the VESTA trademark.

BRIEF DESCRIPTION OF THE PHOTOGRAPH

The accompanying photographs show as nearly true as it is reasonably possible to make the same in color illustrations of this character, typical plants and plant parts of the new cultivar of the present invention. The plants were 12 weeks of age and were grown at Nuaille, Trementines, France, under standard greenhouse conditions which approximate those commonly utilized for the production of decorative pot mums. The plant had been pinched once and had not been disbudded. No growth regulator was utilized.

FIG. 1 illustrates a typical stem;

FIG. 2 illustrates the top view of a typical leaf from the lower part of the stem;

FIG. 3 illustrates the under view of a typical leaf from the lower part of the stem;

FIG. 4 illustrates the top view of a typical leaf from the upper part of the stem;

Figure 15:
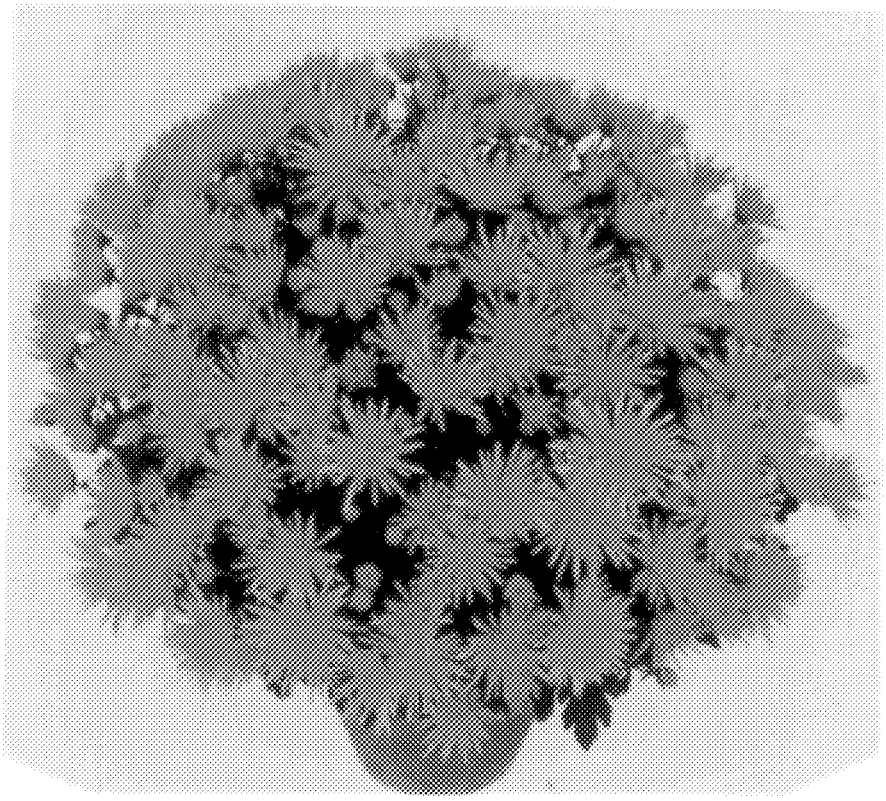

FIG. 5 illustrated the under view of a typical leaf from the upper part of the stem;

FIG. 6 illustrates the side view of a pair of typical unopened buds;

FIG. 7 illustrates the side view of a pair of typical flowers in the course of opening;

FIG. 8 illustrates the top view of a typical open flower;

FIG. 9 illustrates the under view of a typical open flower;

FIG. 10 illustrates the side view of a typical open flower;

FIG. 11 illustrates the top view of three typical outer-ray florets;

FIG. 12 illustrates the under view of three typical outer-ray florets;

FIG. 13 illustrates several typical inner-ray florets which are of very small size; and FIG. 14 illustrates a side of a typical inflorescence with buds and blossoms in various stagtes of opening.

FIG. 15 illustrates a typical whole mature plant while blossoming.

DETAILED DESCRIPTION

The chart used in the identification of colors described hereafter is The R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, were rooted in late May and were stopped in early July. All primary laterals of the plants were retained. The plants were grown outdoors until late September and then were grown in the greenhouse with a minimum temperature of 15.5° C. These conditions approximate those commonly utilized for the production of decorative pot mums.

Classification:

*Botanical.*—*Dendranthema grandiflora.* cv. 'Chabaxo'.

*Commercial.*—Decorative pot mum.

Inflorescence

A. Capitulum:

*Type.*—Double.

*Number of rows of involucral bracts.*—Commonly five or less.

*Diameter across face when grown indoors.*—Approximately 50 to 65 mm. on average for a single blossom when fully expanded.

*Diameter across face when grown outdoors during the autumn.*—Approximately 80 to 100 mm. on average for a single blossom when fully expanded.

*Frequency.*—Corymbiform. The blossoms are borne in the shape of a corymb (i.e., as a substantially flat-topped flower cluster in which the individual stalks grown upward from various points on a main stem to approximately the same height).

*Outside bud coloration.*—Yellow Group 6D with some weak orange tints at the distal one-half.

B. Corolla of ray and disc florets:

*Receptacle.*—Small to medium and conically raised.

*Disc florets.*—Tubular, yellow in coloration, long in overall length, few in number, very difficult to observe, and tend to be scattered among the ray florets with a samll cluster at the apex of the receptacle that is visible only when the ray florets are removed.

*General tonality.*—Yellow.

*Color ray florets.*—When mature the outer side of most ray flroets is Yellow Group 8B, and inner side of most ray florets is between Yellow Group 5A and Yellow Group 6A.

*Configuration ray florets.*—The longitundinal axis of the majority of the ray florets is reflexed weakly along most of the distal one-half. The longitudinal axis of the ray florets from outer rows also commonly is reflexed weakly along most of the axis. The length of the corolla tube from the ray florets is medium and increases to very long in the outer rows. The cross-section of the ray florets is convex, there commonly are two keels, and the ray florets often are spatulate in configuration. The florets with shorter corolla tubes tend to exhibit spatulate ends, and those with very long corolla tubes tend to be quilled at the ends. The ray florets are thin, and their surfaces are textured. The tips of the ray florets are rounded. The ray florets commonly are approximately 3 cm. in length and approximately 0.7 cm. in width on average.

C. Reproductive organs:

*Androecium.*—Generally present with disc florets and absent in ray florets.

*Gynoecium.*—Generally present with most disc florets and with most of the ray florets.

*Pollen.*—Formed in a slight quantity and golden-yellow in coloration.

*Fragrance.*—Typical of Chrysanthemum.

Plant

A. General appearance:

*Height.*—Very short, and approximately 25 to 30 cm. in height on average.

B. Foliage:

*Color.*—Green Group 137C on the upper surface, and Green Group 137D on the under surface.

*Size.*—The size varies with the location on the stem and is substantially influenced by the level of nutrition that is received during the growing period. The length to width ratio commony is greater than 2:1 (as illustrated in FIGS. 2 and 3).

*Configuration.*—Lobed (as illustrated).

*Texture.*—Fleshy.

*Serration.*—Medium.

*Length of lower lobe.*—Medium to long.

*Shape of base of sinus.*—Rounded.

*Shape of base of leaf.*—Obtuse, occasionally asymmetric.

*Claw in base of sinus between lateral lobes.*—Absent.

*Margins of sinus between lateral lobes.*—Converging.

*Apex.*—Mucronate.

*Stems.*—Thin, angular in cross-section, present some brittleness. Yellow-Green Group 146D in coloration, and with anthocyanin colroation in patches alogn the stem.

I claim:

1. A new and distinct cultivar of Chrysanthemum plant named 'Chabaxo', substantially as herein shown and described, which:

(a) exhibits in profusion attractive decorative double yellow blossoms, (b) is highly amenable to branching by pinching, (c) forms attractive foliage, (d) achieves a short plant height, and (e) is particularly well suited for flowering as a pot mum on a recurrent basis throughout the year.

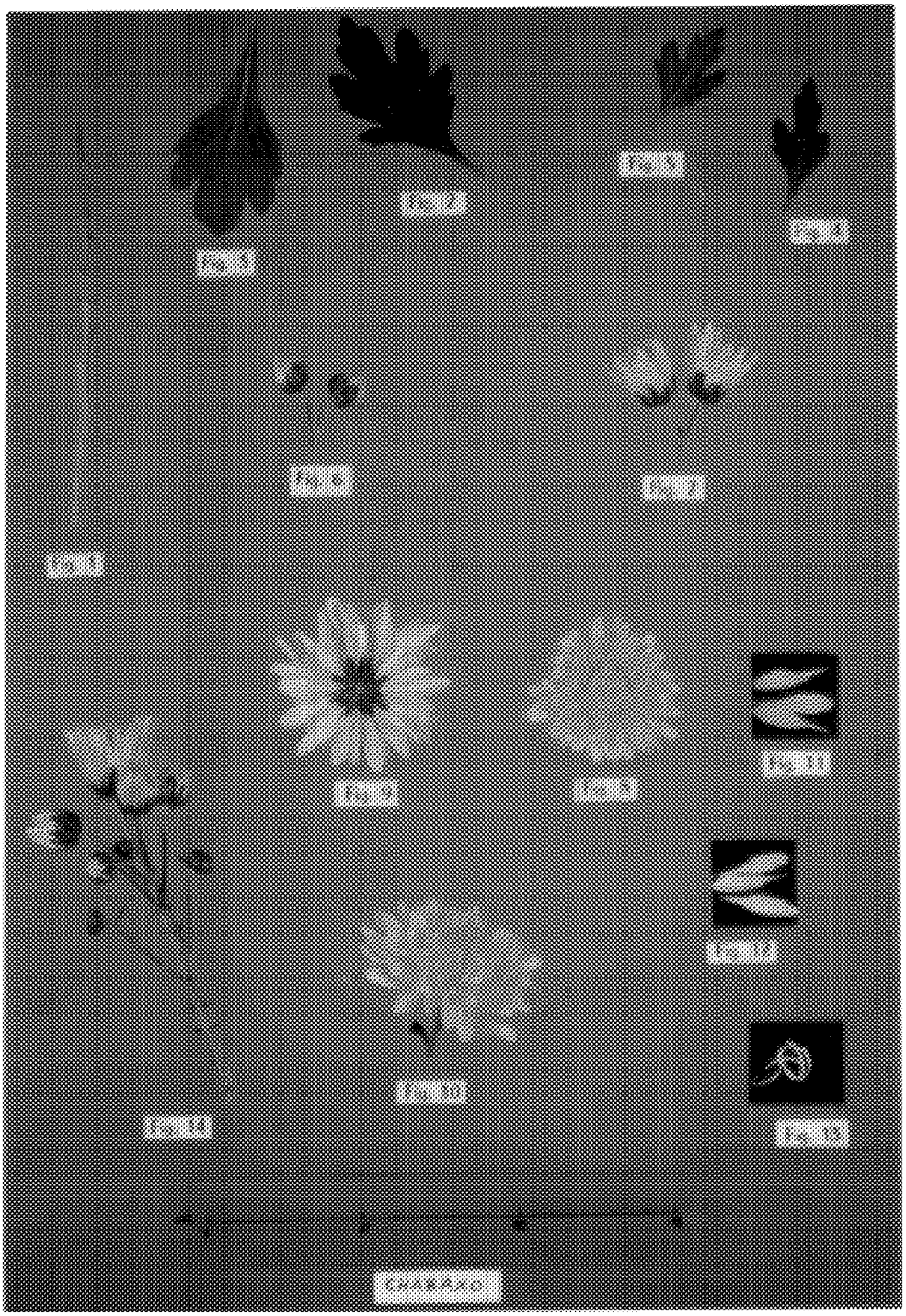

* * * * *